(12) United States Patent
Ahmed et al.

(10) Patent No.: US 10,154,925 B2
(45) Date of Patent: Dec. 18, 2018

(54) INTRAOCULAR DRAINAGE DEVICE

(71) Applicant: NEW WORLD MEDICAL, INC., Rancho Cucamonga, CA (US)

(72) Inventors: Abdul Mateen Ahmed, Claremont, CA (US); Eric Porteous, Corona, CA (US); Suhail Abdullah, Fontana, CA (US); Khalid Mansour, Corona, CA (US); Joey Tran, Ontario, CA (US); Patrick Chen, Hacienda Heights, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 0 days.

(21) Appl. No.: 15/613,021

(22) Filed: Jun. 2, 2017

(65) Prior Publication Data

US 2017/0348151 A1 Dec. 7, 2017

Related U.S. Application Data

(60) Provisional application No. 62/345,723, filed on Jun. 3, 2016, provisional application No. 62/368,990, filed on Jul. 29, 2016.

(51) Int. Cl.
*A61M 5/00* (2006.01)
*A61F 9/007* (2006.01)
*A61L 31/06* (2006.01)

(52) U.S. Cl.
CPC .......... *A61F 9/00781* (2013.01); *A61L 31/06* (2013.01); *A61F 2220/0025* (2013.01); *A61F 2250/0013* (2013.01); *A61F 2250/0029* (2013.01)

(58) Field of Classification Search
CPC ........ A61F 9/00781; A61F 2250/0013; A61M 27/002; A61L 31/06
See application file for complete search history.

(56) References Cited

U.S. PATENT DOCUMENTS

| 5,071,408 | A | * | 12/1991 | Ahmed | A61F 9/00781 604/11 |
| 5,171,213 | A | | 12/1992 | Price, Jr. | |
| 5,338,291 | A | | 8/1994 | Speckman et al. | |
| 5,616,118 | A | * | 4/1997 | Ahmed | A61F 9/00781 604/294 |

(Continued)

FOREIGN PATENT DOCUMENTS

KR 20160030766 A 3/2016

OTHER PUBLICATIONS

International Search Report and Written Opinion for Application No. PCT/US2017/035691, dated Jan. 15, 2018, 17 pages.

*Primary Examiner* — Philip R Wiest
(74) *Attorney, Agent, or Firm* — Morgan, Lewis & Bockius LLP

(57) ABSTRACT

An intraocular drainage device may include a monolithic silicone body having a flap, a rigid bottom plate having a portion configured to contact a corresponding portion of the flap, and a tube having a proximal end disposed between the flap and the rigid bottom plate. The corresponding portion of the flap may be configured to separate from the portion of the rigid bottom plate responsive to a fluid pressure in aqueous humor received from the tube. A plurality of parallel microgrooves may be formed on one or more portions of one or more outer surfaces of the intraocular drainage device.

16 Claims, 9 Drawing Sheets

(56) References Cited

U.S. PATENT DOCUMENTS

| | | | | |
|---|---|---|---|---|
| 5,681,275 A | * | 10/1997 | Ahmed | A61F 9/00781 604/8 |
| 5,752,928 A | | 5/1998 | de Roulhac et al. | |
| 5,785,674 A | * | 7/1998 | Mateen | A61M 27/002 604/8 |
| 6,261,256 B1 | | 7/2001 | Ahmed | |
| 7,357,778 B2 | * | 4/2008 | Bhalla | A61F 9/00781 604/264 |
| 8,632,489 B1 | * | 1/2014 | Ahmed | A61F 9/00781 604/8 |
| 2002/0087111 A1 | | 7/2002 | Ethier et al. | |
| 2004/0215126 A1 | * | 10/2004 | Ahmed | A61F 9/00781 604/9 |
| 2010/0042209 A1 | * | 2/2010 | Guarnieri | A61F 9/00781 623/4.1 |
| 2011/0071458 A1 | * | 3/2011 | Rickard | A61F 9/00781 604/9 |
| 2013/0150777 A1 | * | 6/2013 | Bohm | A61F 9/00781 604/9 |
| 2013/0261530 A1 | | 10/2013 | Yalamanchili | |
| 2014/0364789 A1 | | 12/2014 | Schaller | |
| 2015/0057592 A1 | * | 2/2015 | Gunn | A61F 9/00781 604/9 |
| 2015/0202082 A1 | * | 7/2015 | Ilios | A61F 9/00781 604/9 |
| 2016/0242962 A1 | * | 8/2016 | Torello | A61F 9/00781 |
| 2016/0302967 A1 | * | 10/2016 | Ahn | A61F 9/00781 |

\* cited by examiner

INTRAOCULAR DRAINAGE DEVICE

CROSS-REFERENCE TO RELATED APPLICATIONS

The present application claims the benefit of priority under 35 U.S.C. § 119 to U.S. Provisional Patent Application Ser. No. 62/345,723 entitled "INTRAOCULAR DRAINAGE DEVICE" filed on Jun. 3, 2016, and U.S. Provisional Patent Application Ser. No. 62/368,990 entitled "INTRAOCULAR DRAINAGE DEVICE WITH MICROGROOVES" filed on Jul. 29, 2016, the disclosure of each of which is hereby incorporated by reference in its entirety for all purposes.

TECHNICAL FIELD

The present disclosure generally relates to intraocular devices and, in particular, relates to intraocular drainage devices.

BACKGROUND

Aqueous humour typically drains from the anterior chamber of the eye via the trabecular meshwork at the edge of the cornea. However, in some circumstances, overproduction of aqueous humour or reduced drainage of aqueous humour can increase intraocular pressure which can cause discomfort and/or damage the optic nerve. Accordingly, it would be desirable to be able to provide increased drainage of aqueous humour from the anterior chamber, particularly for glaucoma patients.

SUMMARY

In accordance with various aspects of the disclosure, an intraocular drainage device may include a main body, an internal flap, a rigid bottom plate having a portion configured to contact a corresponding portion of the flap, a rigid top plate, and a tube having a proximal end disposed between the flap and the rigid bottom plate. The main body may be a rigid main body or a flexible main body. In one implementation that is sometimes described herein as an example, the main body and the flap may, for example, be formed from a monolithic silicone body having an integral flap. However, this is merely illustrative. In other implementations, a flexible main body such as a monolithic flexible main body may be formed from biocompatible flexible materials other than silicone. In yet other implementations, the main body may be formed from a rigid material such as a plastic. For example, in some implementations, the main body, the rigid bottom plate and the rigid top plate may be formed from a common material.

The corresponding portion of the flap may be configured to separate from the portion of the rigid bottom plate responsive to a pressure from aqueous humor received from the tube. The tube can have a distal end configured to be extended through the sclera of a patient's eye and into the anterior chamber of the eye. The silicone body and the rigid bottom plate may form a chamber that is fluidly coupled to a lumen in the tube so that, in operation, aqueous can flow from the anterior chamber of the eye, through the lumen, to the chamber formed by the silicone body and the rigid bottom plate.

When aqueous fills the chamber formed by the silicone body and the rigid bottom plate, fluid pressure from the aqueous can bear against the corresponding portion of the flap causing the corresponding portion of the flap to separate from the portion of the rigid bottom plate to generate a fluid flow path out of the chamber. The fluid flow path may extend through a channel between the rigid bottom plate and the rigid top plate and through an opening such as a slot in the silicone body.

The silicone body, the rigid bottom plate, and the rigid top plate may be coupled together and sutured in place between the sclera and the conjunctiva of the patient's eye. In this configuration, aqueous that flows out of the fluid flow path through the opening in the silicone body may diffuse into the patient's tissues surrounding the device.

The chamber formed by the silicone body and the rigid bottom plate may be disposed between an additional portion of the flap and an additional corresponding portion of the rigid bottom plate. The rigid bottom plate may include a first channel adjacent the chamber and a second channel. The first channel may be disposed on a first side of the portion of the flap and the second channel may be disposed on an opposing second side of the flap to form a portion of the fluid flow path. The rigid top plate may include a channel disposed opposite the second channel of the bottom plate to form a portion of the fluid flow path. The flap may include a recess configured to receive a portion of the tube. The additional corresponding portion of the flap may be disposed between the portion of the flap and the recess.

The rigid top plate and rigid bottom plate may be engaged at one or more locations via one or more corresponding openings in the flap. The rigid bottom plate and/or the rigid top plate may be formed from plastic such as a polysulfone plastic.

Outer surfaces of the main body, the rigid bottom plate, and/or the rigid top plate may be provided with one or more microgrooves. The intraocular drainage device may include a plurality of microgrooves on one or more outer surfaces of the device. The microgrooves may include a plurality of microgrooves that run in parallel rows from a front portion to a back portion of the device on the top and bottom surfaces of the device. The intraocular drainage device may include one or more substantially vertical surfaces such as sidewall surfaces connecting the top and bottom surface. The substantially vertical surfaces may be provided with one or more parallel microgrooves arranged in rings around the circumference of the device like steps on a ladder.

In some aspects, the microgrooves may be arranged in one or more of various patterns as described herein for contact guidance of cells and/or tissues surrounding the intraocular device. Contact guidance may refer to an in vivo effect described by the Dictionary of Cell and Molecular Biology as "directed locomotory response of cells to an anisotropy of the environment, for example the tendency of fibroblasts to align along ridges or parallel to the alignment of collagen fibres in a stretched gel."

Although microgrooves on an intraocular implant having a main body, a rigid bottom plate, and a rigid top plate, are sometimes described herein as an example, other intraocular drainage devices can be provided with microgrooves. For example, microgrooves that extend longitudinally in a direction from a front of the device to the rear of the device on top and bottom surfaces, radial microgrooves, circumferential and parallel sidewall microgrooves, and/or other suitable microgroove patterns for, for example, contact guidance for cell and tissue formation may be provided on the exterior surfaces of intraocular drainage devices such as those described in U.S. Pat. Nos. 5,411,473, 5,616,118, 5,681,275, 5,785,674, 6,261,256, and/or 7,025,740, all of which are incorporated herein by reference in their entireties.

In accordance with some aspects of the subject disclosure, an intraocular drainage device is provided that includes a monolithic silicone body having a flap, a rigid bottom plate having a portion configured to contact a corresponding portion of the flap, and a tube having a proximal end disposed between the flap and the rigid bottom plate. The corresponding portion of the flap is configured to separate from the portion of the rigid bottom plate responsive to a pressure of aqueous humor received from the tube.

In accordance with some aspects of the subject disclosure, an intraocular drainage device is provided that includes a main body having a channel, a flap disposed within the main body, a rigid bottom plate having a portion configured to contact a corresponding portion of the flap, and a tube bonded to the main body such that the channel is configured to guide fluid from the tube to a chamber formed adjacent the flap. The corresponding portion of the flap is configured to separate from the portion of the rigid bottom plate responsive to a pressure of the fluid in the chamber.

In accordance with some aspects of the subject disclosure, an intraocular drainage device is provided that includes a main body, a flow control device within the main body operable to allow fluid flow through the main body in a fluid flow direction, and a plurality of microgrooves formed on an outer surface of the main body, the plurality of microgrooves being arranged in parallel rows and extending substantially parallel to the fluid flow direction from a front end to a back end of the main body.

In accordance with some aspects of the subject disclosure, an intraocular drainage device is provided that includes a flexible main body having a flap and a top surface having an opening bounded by opposing lobes, a rigid bottom plate having a portion configured to contact a corresponding portion of the flap, and a rigid top plate disposed in the opening in the top surface of the flexible main body. A portion of the top surface of the rigid top plate in the opening forms a portion of a top surface of the device and the opposing lobes each bear against another portion of the top surface of the rigid top plate.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
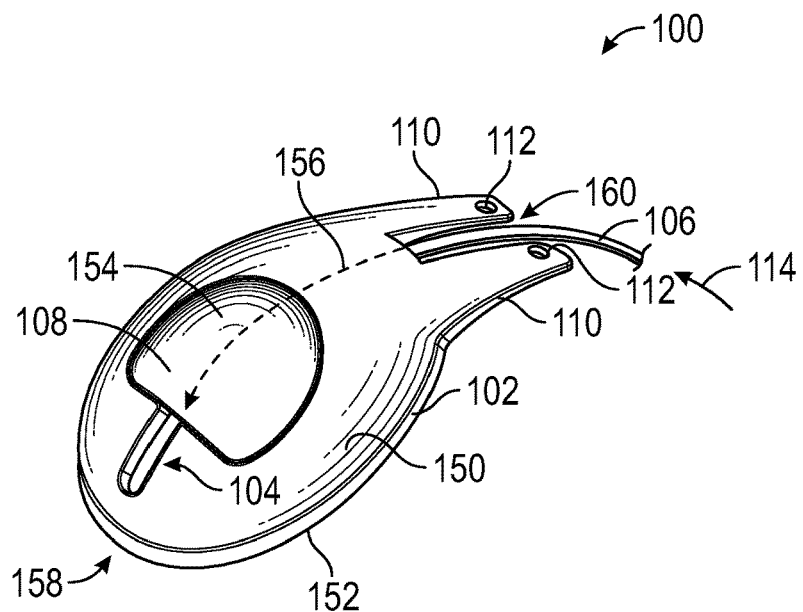
FIG. 1 shows a perspective view of an intraocular drainage device, in accordance with one or more embodiments of the present disclosure.

According to some embodiments, for example as shown in FIG. 1, an intraocular device such as intraocular drainage device 100 can include a main body 102 such as a relatively flexible main body and a relatively rigid top plate 108 disposed in an opening in a top surface of the main body. Although various examples are described herein in which main body 102 is a flexible main body (e.g., a silicone body or a flexible main body formed from other biocompatible flexible materials), other implementations with a rigid main body 102 are contemplated. Flexible main body 102 may include an outlet port 104. Intraocular drainage device 100 may also include an input tube 106 having a lumen (not visible in FIG. 1). A valve within flexible main body 102 may be operable to controllably couple the lumen of tube 106 with an outlet port such as outlet port 104 located at or near a back end 158 of main body 102.

Rigid top plate 108 may be formed, for example, from a rigid plastic such as polysulfone plastic. Flexible main body 102 may be a monolithic flexible body formed, for example, from silicone or other suitable flexible materials. In the example of FIG. 1, outlet port 104 is formed from slot in the top surface of main body 102 adjacent top plate 108. However, this is merely illustrative. In other embodiments, outlet port 104 may be a round, square, oval, multi-leaf, v-shaped, or other-shaped opening in flexible body 102 and/or may be formed at other locations (e.g., spaced apart from top plate 108 or partially or completely disposed on an edge of main body 102. In other embodiments, more than one outlet port may be formed in main body 102 and/or other components of device 100 such as top plate 108.

As shown in FIG. 1, main body 102 may include a pair of extensions such as arms 110 that extend along opposing sides of a portion of tube 106. Arms 110 may be configured to extend from main body 102, at the front end 160 of main body 102, in the direction of the anterior of a patient's eye. Each arm 110 may include one or more features that facilitate securement of device 100 to the eye of the patient. In the example of FIG. 1, each arm 110 includes an opening 112 for suturing of main body 102 to the patient's eye. Each arm 110 may have a thickness that is substantially the same as the thickness of tube 106. Extending arms 110 may allow suturing of device 100 at a location closer to the limbus of the eye than in conventional devices which may facilitate easier implantation for a surgeon.

Intraocular device 100 may be surgically implanted between the sclera and the conjunctiva of the eye of a patient such that fluid such as aqueous humor that flows through device 100 (e.g., in a fluid flow direction as indicated by arrow 156) and out from outlet port 104 forms a bleb on and/or around the outer surface of device 100 that can be absorbed the surrounding tissue (e.g., via the scleral venous system). The outer surface of device 100 may include a top surface 150 of main body 102, a top surface 154 of top plate 108, and a sidewall surface 152 of main body 102 that extends between top surface 150 and a bottom surface (not visible in FIG. 1) of main body 102. The outer surface of device 100 may also include the bottom surface of main body 102 and a bottom surface of a bottom plate (not visible in FIG. 1) disposed in an opening in the bottom surface of main body 102. As discussed in further detail hereinafter, following implantation, intraocular device 100 may be configured such that the bottom surface of main body and the bottom surface of the bottom plate rest against the sclera of the patient's eye and such that the top surface 150 of main body 102 and the top surface 154 of top plate 108 rest against the conjunctiva of the patient's eye. As discussed in further detail below in connection with, for example, FIGS. 6 and 7, one or more portions of the outer surface of device 100 may include microgroove patterns that aid the healing response of the eye and may also improve the functioning of the device over time following implantation.

Tube 106 may be fluidly coupled, at a proximal end (e.g., proximal to main body 102 relative to a distal end of the tube), to a chamber within main body 102. As shown in FIG. 1, tube 106 may extend from a front end 160 of main body 102 at a location between arms 110 toward the anterior of the patient's eye. A distal end of tube 106 may be configured to be disposed within an anterior chamber of the eye of a patient so that fluid such as aqueous humor can enter a lumen of the tube 114 and controllably flow through the lumen to the chamber. A portion of tube 106 is configured to extend through a portion of the sclera of the eye of the patient at a location between the proximal end and the distal end so that the distal end of tube 106 can reach the anterior chamber.

In some embodiments, device 100 may be provided with a removable cannula that can be used for flushing of device 100 prior to surgical implantation.

Figure 2:
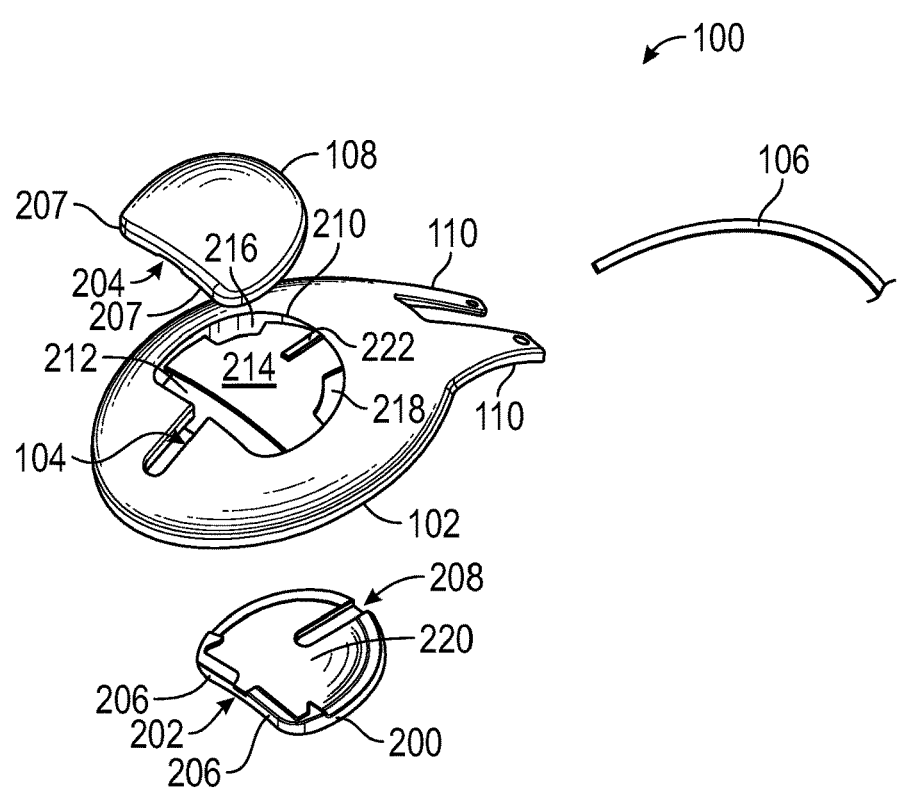
FIG. 2 shows an exploded perspective view of the intraocular drainage device of FIG. 1, in accordance with one or more embodiments of the present disclosure.

Turning now to the exploded perspective view of device 100 in FIG. 2, features of main body 102 and a rigid bottom plate 200 that form a chamber and a valve to control fluid flow from tube 106 to outlet port 104 can be seen. For example, main body 102 may include a flap 214 that extends laterally across the interior of main body 102. In an assembled configuration for device 100 (e.g., the assembled configuration shown in FIG. 1), flap 214 may be configured to seat against a top or interior surface 220 of bottom plate 200 to form a valve with a disengageable seal. Flap 214 may be a silicone flap having a thickness of less than about one five-thousandth of an inch (for example).

In the assembled configuration, tube 106 may extend at least partially into a channel 208 in bottom plate 200. A top surface of tube 106 may seat at least partially within a recess 222 of main body 102. In this way, tube 106 may be secured within channel 208 (e.g., by a sealing compression caused by top plate 108 and bottom plate 200) such that the lumen of the tube is in fluid communication with a chamber formed by a portion of channel 208 and flap 214. However, this is merely illustrative.

In other implementations, tube 106 may be bonded to main body 102. In this implementation, main body 102 may have a channel therewithin configured guide fluid from tube 106 to a chamber such as chamber 304 under flap 214.

In various implementations, the portion of flap 214 that seats against top surface 220 of bottom plate 200 may separate from surface 220 responsive to a pressure of aqueous humor received in the chamber, thereby allowing aqueous to flow between flap 214 and top surface 220.

Bottom plate 200 may include an additional channel 202 formed between ridges 206. Channel 202 of bottom plate 200 may, in an assembled configuration, be disposed opposite a corresponding channel 204 of top plate 108. Channel 204 of top plate 108 may be formed between ridges 207. Ridges 207 of top plate 108 may engage with ridges 206 of bottom plate 200 within an internal opening 212 within main body 102. For example, during assembly of device 100, top plate 108 may be placed into an opening 210 in a top surface of main body 102 and bottom plate 200 may be placed into an opening in a bottom surface of main body 102 such that ridges 206 of bottom plate 200 and ridges 207 of top plate 108 meet within opening 212 proximal to flap 214. Ridges 207 of top plate 108 and ridges 206 of bottom plate 200 may be secured together mechanically, adhesively, or may be ultrasonically welded together (for example) to secure top plate 108 to bottom plate 200 with flap 214 secured therebetween.

Additional portions of top plate 108 and bottom plate 200 may be engaged together (e.g., mechanically, adhesively, or using an ultrasonic weld) within additional internal openings in main body 102 such as openings 216 and 218, each disposed on a distal side of flap 214. Bottom plate 200 may be formed, for example, from a rigid plastic such as polysulfone plastic.

During assembly operations for device 100, tube 106 may be provided between bottom plate 200 (e.g., within a portion of channel 208) and recess 222 of main body 102 such that, when top plate 108 and bottom plate 200 are secured together, tube 106 is secured between bottom plate 200 and main body 102. Opposing channels 202 and 204 may form an exit port within device 100 that is fluidly coupled with outlet port 104.

Figure 3:
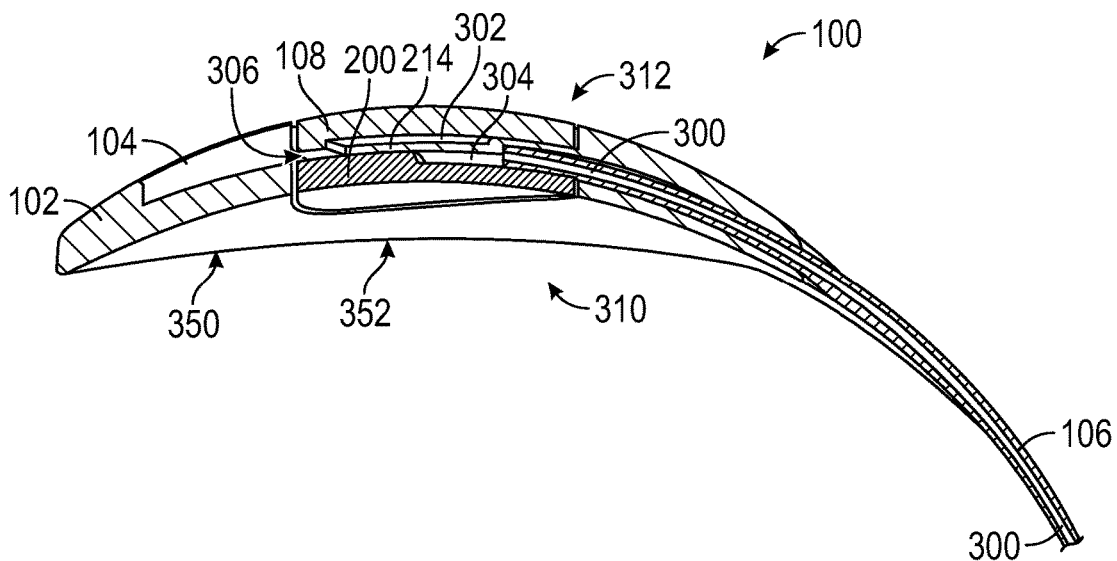
FIG. 3 shows a cross-sectional side view of the intraocular drainage device of FIG. 1, in accordance with one or more embodiments of the present disclosure.

FIG. 3 shows a cross-sectional side view of intraocular device 100 in which various additional features of device 100 can be seen. For example, as shown in FIG. 3, tube 106 may include a lumen 300 in fluid communication with a chamber 304 formed between a portion of bottom plate 200 and flap 214 (e.g., within a portion of channel 208 of FIG. 2). In operation, when fluid pressure within chamber 304 (e.g., due to aqueous humor received from the anterior chamber of a patient's eye via lumen 300) reaches a predetermined pressure threshold, the portion of flap 214 that is seated against bottom plate 200 may be moved away from bottom plate 200 to allow fluid to flow therebetween to an exit port 306 formed between top plate 108 and bottom plate 200 (e.g., by opposing channels 202 and 204 of FIG. 2).

In the example of FIG. 3, an additional chamber 302 is shown between a top surface of flap 214 and a bottom or interior surface of top plate 108. Chamber 302 may provide space into which flap 214 can move when displaced from bottom plate 200 by fluid pressure in chamber 304. Chamber 302 may be in fluid communication with exit port 306 such that fluid that flows from exit port 306 can flow out of device 100 through outlet port 104 and/or into chamber 302. However, this is merely illustrative. In other implementations, chamber 302 may be prevented from receiving fluid that flows between flap 214 and bottom plate 200 from chamber 304 and/or prevented from receiving any fluid from outside of device 100 (e.g., via outlet port 104.

For example, in FIG. 3, a proximal end of flap 214 is shown spaced apart from the exit port 306 formed by channels 202 and 204. However, in other implementations, the proximal end of flap 214 may extend to or partially into the exit port 306 formed by channels 202 and 204 such that flap 214 itself blocks fluid flow into chamber 302 while still allowing fluid flow out of chamber 304 to outlet port 104 when flap 214 is displaced from bottom plate 200. In other implementations, additional flow control structures may be provided that block flow of fluids into chamber 302.

It can also be seen in FIG. 3 that main body 102 may be a monolithic (e.g., molded) body in which flap 214 is integrally and continuously formed with other portions of the main body. However, this is merely illustrative. In other configurations, flap 214 may be a separate flap formed within main body 102.

As shown in the example of FIG. 3, in the assembled configuration, bottom plate 200 and the bottom surface of main body 102 may form a bottom concave surface 310 for device 100 having a shape configured to conform to the convex shape of the sclera of the patient's eye. Bottom concave surface 310 may be formed by bottom surface 350 of main body 102 and bottom surface 352 of bottom plate 200. In the assembled configuration, top plate 108 and the top surface of main body 102 may form a top convex surface 312 for device 100 having a shape configured to conform to the concave interior shape of the conjunctiva of the patient's eye.

Figure 4:
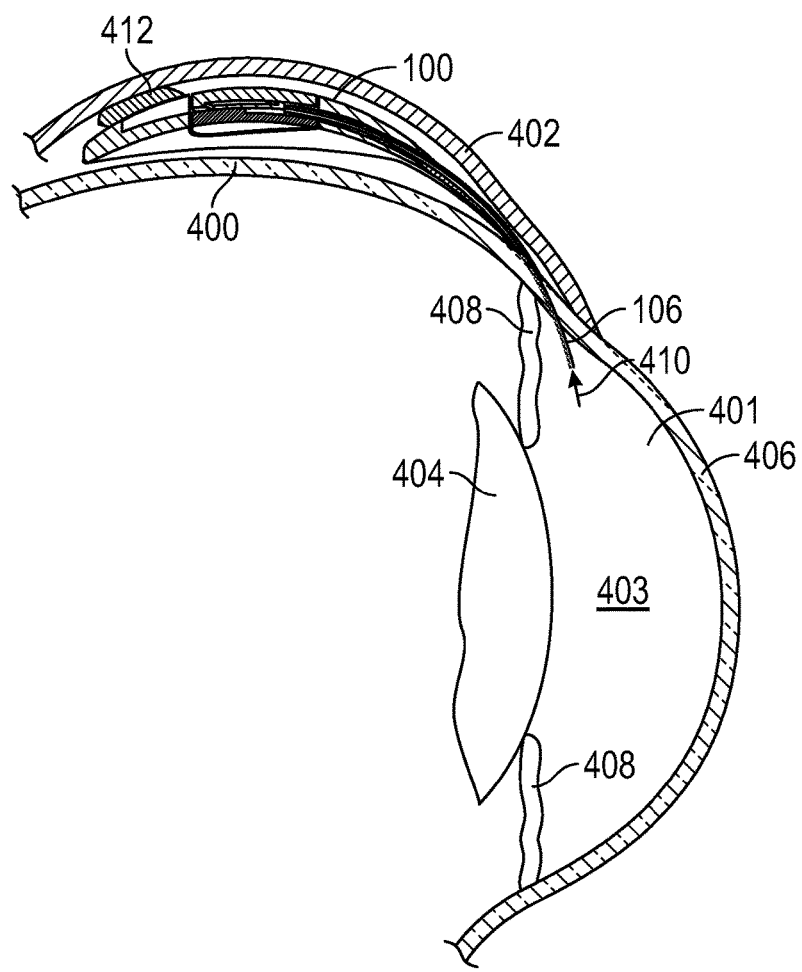
FIG. 4 shows a cross-sectional side view of the intraocular drainage device of FIG. 1 in situ in an eye of a patient, in accordance with one or more embodiments of the present disclosure.

FIG. 4 schematically shows a cross-sectional view of intraocular drainage device 100 disposed in situ in a patient's eye such that main body 102, assembled with top and bottom plates 108 and 200 is disposed between the sclera 400 and conjunctiva 402 of the patient's eye. As shown, tube 106 may extend through sclera 400 so that aqueous humor 403 in the anterior chamber 401 of the eye (bounded in part by cornea 406, lens 404 and iris 408) can flow into the lumen of tube 106 (as indicated by arrow 410).

As shown in FIG. 4, fluid that has flowed through the valve formed within device 100 by flap 214 and bottom plate 200 may form a bleb 412 on and/or around device 100 that can be absorbed into the patient's tissue. In this way, excess fluid pressure in anterior chamber 401 associated with a glaucoma condition may be relieved.

Figure 5:
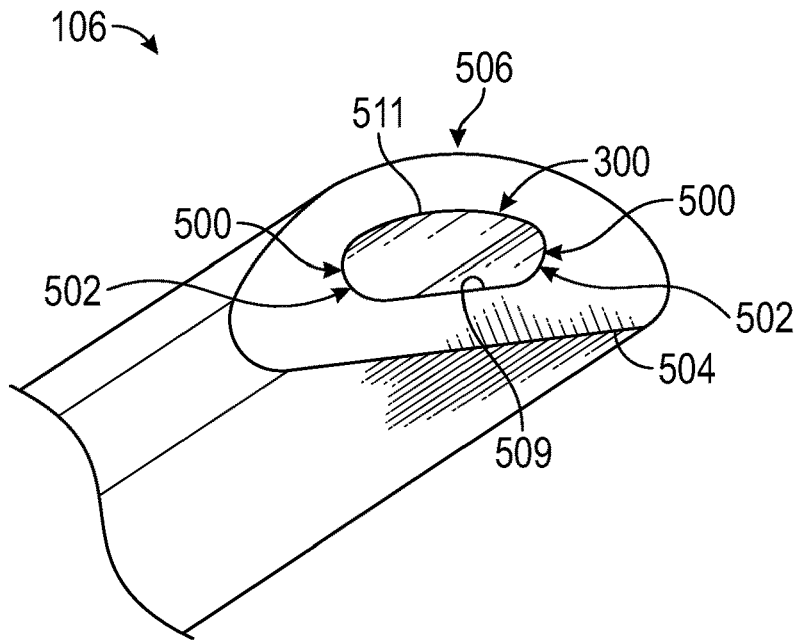
FIG. 5 shows a cross-sectional perspective view of a tube of an intraocular drainage device, in accordance with one or more embodiments of the present disclosure.

FIG. 5 is a cross-sectional perspective view of a portion of tube 106. In the example of FIG. 5, tube 106 has a D-shaped cross-sectional profile. A D-shaped cross-sectional profile may provide archways 502 along sidewalls 500 of lumen 300 that prevent kinking or crushing of lumen 300.

Moreover, the D-shaped profile of tube 106 may provide a relatively flat bottom surface 504 of tube 106 for resting against the sclera of the patient's eye and may provide a top surface 506 having a relatively large radius of curvature (e.g., relative to the radius of curvature of a cylindrical tube) that reduces the stress point at which the conjunctiva of the eye interfaces with tube 106. A relatively flat bottom surface 504 and a relatively large radius of curvature top surface 506 may reduce the stress on the underlying sclera and the overlaying conjunctiva due to the presence of tube 106 and may provide a substantially thinner tube (e.g., a tube with a thickness of less than about 20 thousandths of an inch or between 12 and 16 thousandths of an inch). Lumen 300 may have a bottom surface 509 that is substantially flat and substantially parallel to bottom surface 504. Lumen 300 may have a top surface 511 having a radius of curvature that corresponds to the radius of curvature of top surface 506 so that top surface 511 and top surface 506 are substantially parallel. Top surface 511 and bottom surface 509 of lumen 300 each run between sidewalls 500.

A low profile tube such as the D-shaped tube of FIG. 5 may help reduce or eliminate the need for a graft of a patch of tissue over tube 106 that protects the conjunctiva. However, this is merely illustrative and tube 106 may be covered with patch graft in some scenarios.

In some implementations, one or more portions of one or more outer surfaces of an intraocular drainage device may be provided with one or more grooves such as microgrooves. In some implanted medical devices, surface patterning can be used to enhance, or prevent, cell or bacterial attachment to the implanted device. For example, in some devices a Sharklet™ pattern can be used to deter bacterial growth.

However, in some embodiments disclosed herein, microgroove patterns such as parallel front-to-back top and bottom surface patterns, radial patterns, circumferential sidewall patterns and/or other suitable microgroove patterns may be provided, not to prevent attachment with a surface, but to help organize cells into a controlled alignment along the implant. For example, the micro-grooves may align rows of cells along the microgrooves and/or align individual cells (e.g., by causing elongation of an individual cell and/or individual cell nucleus) along the microgrooves. For example, the microgrooves may facilitate contact guidance and/or other effects that cause alignment of the rows of cells or individual cells.

Figure 6:
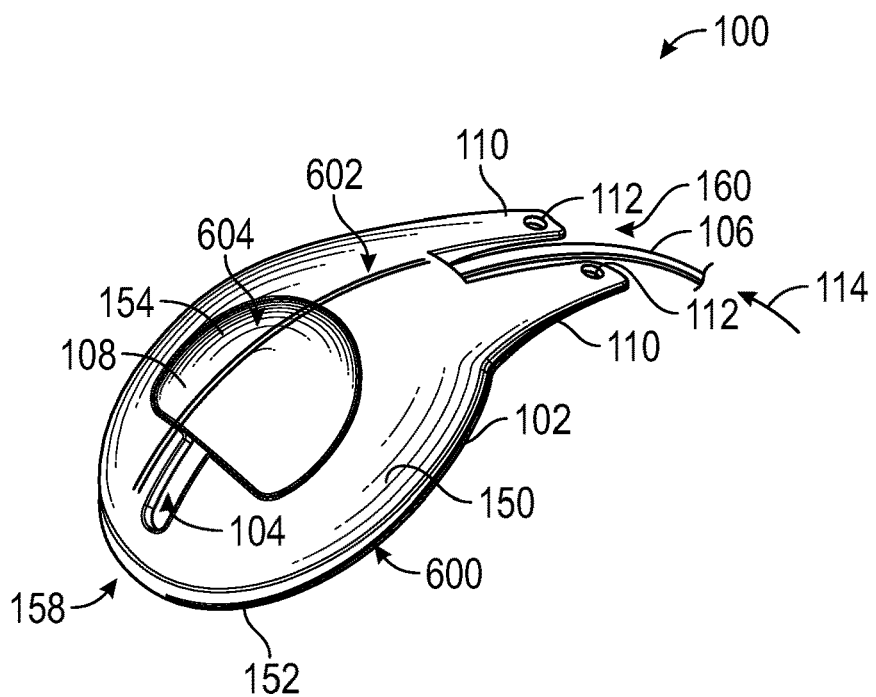
FIG. 6 shows a perspective view of an intraocular drainage device having microgrooves, in accordance with one or more embodiments of the present disclosure.

FIG. 6 shows exemplary microgrooves that may be formed on intraocular drainage device 100 as described herein, in accordance with some embodiments. However, it should be noted that FIG. 6 is merely illustrative and microgroove patterns as described herein can be provided on the outer surfaces of other intraocular drainage devices and other implants.

As shown in FIG. 6, intraocular drainage device 100 may include one or more microgrooves 602 that extend along the top surface of device 100 along the direction 156 (see FIG. 1) of fluid flow within the device from front end 160 toward back end 158. Microgrooves 602 may run in parallel rows along the top surface of device 100. In the example of FIG. 6, two parallel microgrooves are shown on the top surface. However, this is merely illustrative. In other implementations, one, two, three, four, tens, hundreds, or thousands of microgrooves 602 may be formed in parallel rows that substantially cover the entire top surface of device 100.

Circumferential grooves 600 may also be formed on a sidewall of device 100 (e.g., on sidewall 152 of main body 102). Although circumferential grooves 600 are shown extending around only a portion of the circumference of sidewall 152, this is merely illustrative. In various embodiments, grooves 600 may extend around substantially the entire circumference of main body 102 or any portion thereof.

In the example of FIG. 6, three parallel microgrooves 600 are shown on the sidewall surface. However, this is merely illustrative. In other implementations, microgrooves 600 may be formed in parallel rows that substantially cover the entire sidewall surface of device 100.

As shown in FIG. 6, microgrooves 602 may include a portion 604 that runs along the top surface 154 of top plate 108 in some embodiments. For example, portion 604 of microgrooves 602 may be formed such that a subset of microgrooves 602 each includes front and back groove portions formed on surface 150 of main body 102 and includes a portion formed on top surface 154 that extends between the front and back groove portions on surface 150 to form a substantially continuous groove across the multiple components (e.g., across main body 102 and top plate 108).

Although bottom surface 350 of main body 102 and bottom surface 352 of bottom plate 200 (see, e.g., FIG. 3) are not shown in FIG. 6, it should be appreciated that bottom surface 310 may also include one or more microgrooves that extend along the bottom surface 310 of device 100 along the direction 156 (see FIG. 1) of fluid flow from front end 160 toward back end 158. Microgrooves on bottom surface 310 may run in parallel rows along the bottom surface 310 of device 100.

Microgrooves formed on bottom surface 310 may include a portion that runs along the bottom surface 352 of bottom plate 200 in some embodiments. For example, a portion of the microgrooves on bottom surface 310 may be formed such that a subset of the bottom surface microgrooves each includes front and back portions formed on surface 350 of main body 102 and includes a portion formed on bottom surface 352 that extends between the front and back portions on surface 350 to form a substantially continuous groove across the multiple components (e.g., main body 102 and bottom plate 200).

Figure 7:
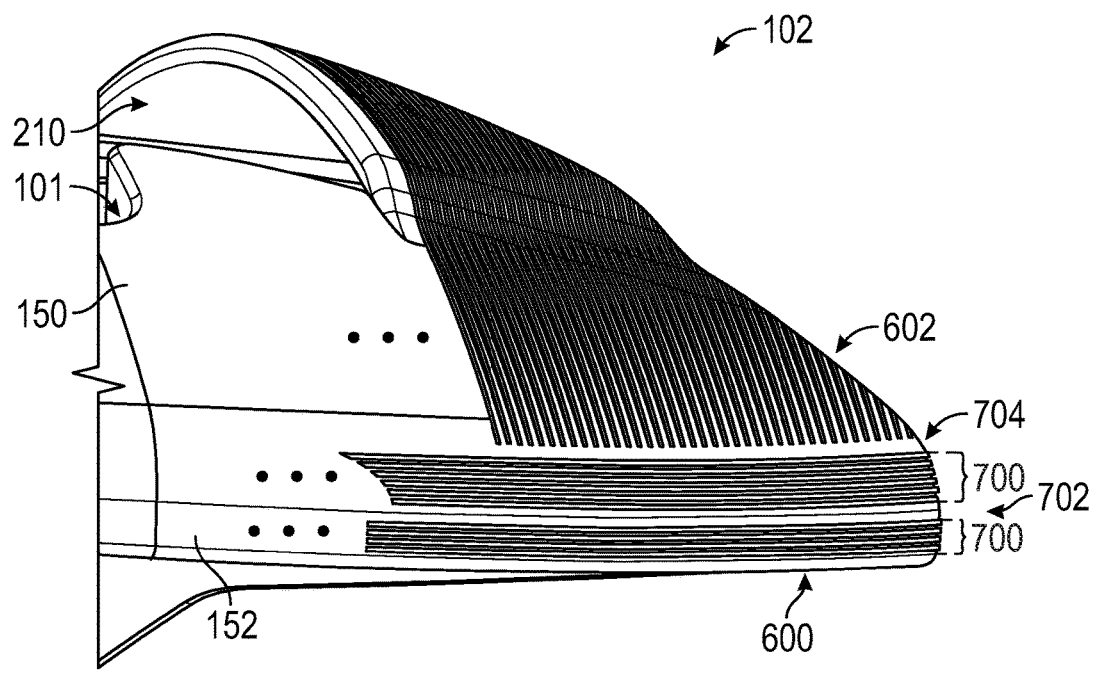
FIG. 7 shows a perspective view of portion of the intraocular drainage device having microgrooves of FIG. 6, in accordance with one or more embodiments of the present disclosure.

FIG. 7 shows an enlarged view of a portion of main body 102 showing microgrooves 600 and 602 formed thereon. In the example of FIG. 7, microgrooves 600 and 602 each only cover a portion of respective top surface 150 and sidewall surface 152, however this is merely illustrative. In other implementations, microgrooves 600 and 602, along with microgrooves formed on bottom surface 310, may cover substantially all of the outer surface of device 100 (including substantially all of the outer surface of main body 102 and, if desired, tube 106 including some or all of top surface 506 and bottom surface 504 of tube 106).

As shown in FIG. 7, microgrooves such as microgrooves 600 and 602 may be formed in equally-spaced rows of microgrooves. Each microgroove may have a width, a depth, and a separation from an adjacent microgroove, each of approximately between 10 and 40 microns (e.g., a width, a depth, and a separation each substantially equal to 25 microns in one implementation). As shown in FIG. 7, in some embodiments, circumferential grooves 600 on sidewall 152 may be formed in sets 700 of microgrooves, the sets 700 being separated by a gap 702 within which the surface of sidewall 152 is substantially smooth.

Because, in situ, sidewall 152 may be arranged substantially vertically with respect to the surface of the patient's eye (e.g., the scleral surface), the circumferential arrangement of grooves 600 shown in FIG. 7 may help to prevent travel of patient cells downward along the sidewall surface toward the eyeball. As shown in FIG. 7, a substantially smooth gap 704 may be provided between grooves 600 and 602 in some implementations.

Figure 8:
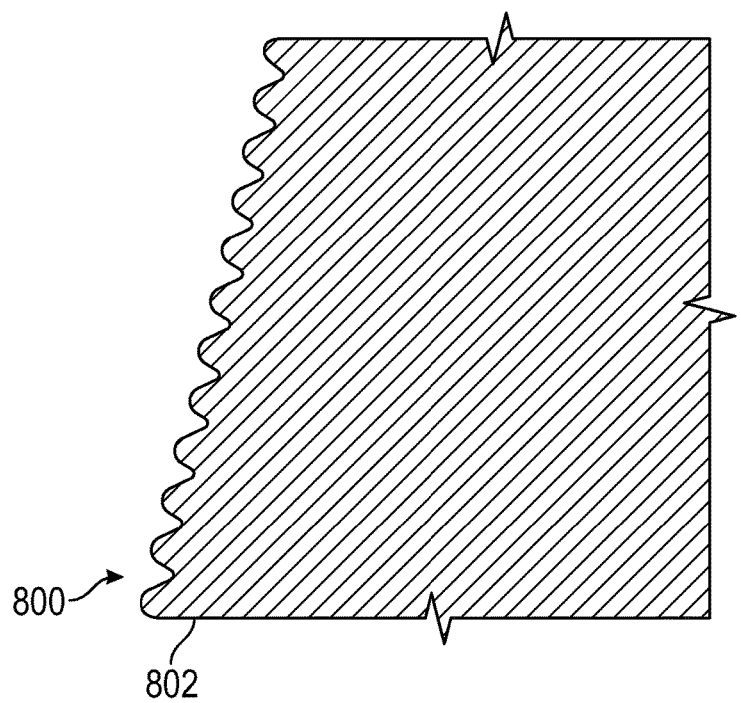
FIG. 8 shows a cross-sectional side view of a portion of an implantable device having microgrooves, in accordance with one or more embodiments of the present disclosure.

FIG. 8 shows an exemplary cross-sectional side view of microgrooves 800 formed on an outer surface of an implantable device 802 (e.g., an implementation of intraocular drainage device 100). Microgrooves 800 may be formed, for example, by laser patterning the surface of a component. In the example of FIG. 8, microgrooves 800 each have a depth of 25 microns, a width at an upper edge of 25 microns and a spacing of 17 microns. However, this is merely illustrative. As previously noted, each microgroove may have a width, a depth, and a separation from an adjacent microgroove, each of approximately between 10 and 40 microns. In the example, of FIG. 8, microgrooves 800 have angled (e.g., non-parallel) sidewalls that converge in a substantially concave bottom surface. However, this is merely illustrative. In other implementations, microgrooves may have parallel sidewalls, planar bottom surfaces, convex or concave sidewalls, a convex bottom surface or any combination thereof (as examples).

Microgrooves on an intraocular drainage device as described herein in connection with various embodiments and implementations may improve organization of fibroblasts and decrease fibrosis for implanted devices, which may help prevent, for example, encapsulation of the implanted device that could otherwise prevent absorption of aqueous around the device, thereby reducing the lifetime and/or effectiveness of the device.

Figure 9:
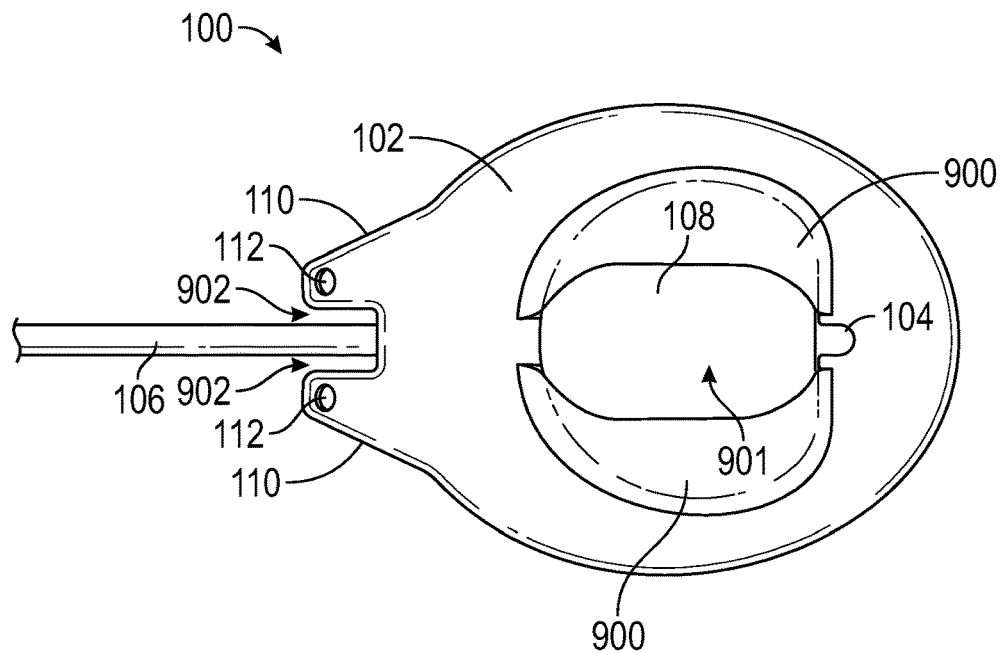
FIG. 9 shows a top view of an intraocular drainage device, in accordance with one or more embodiments of the present disclosure.
Figure 10:
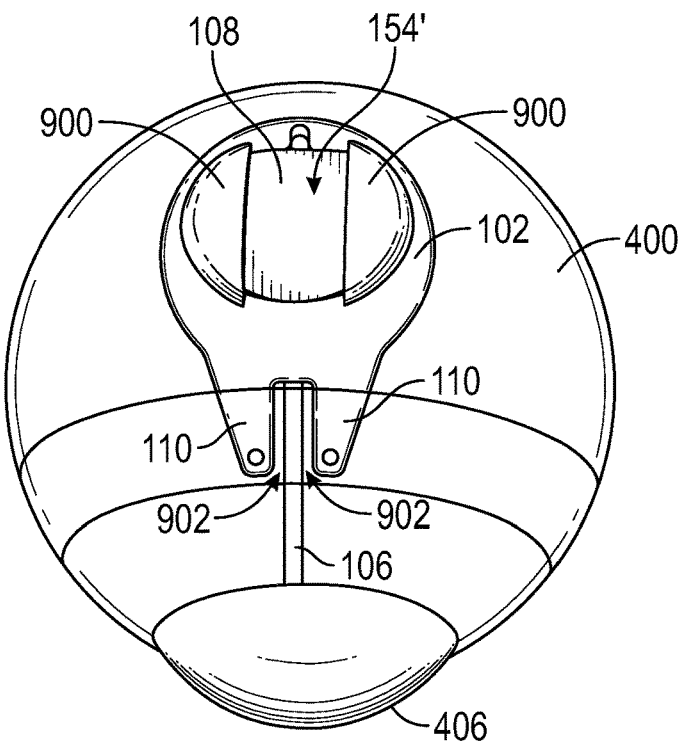
FIG. 10 shows a perspective view of an intraocular drainage device in situ, in accordance with one or more embodiments of the present disclosure.

Although various examples of intraocular drainage device 100 have been described in which top plate 108 is disposed in an opening 210 in main body 102 that has a size and shape that match the size and shape of top plate 108, this is merely illustrative. In various implementations, top plate 108 may be inserted into an opening in main body 102 that is smaller than top plate 108. FIGS. 9 and 10 show exemplary views of an intraocular drainage device 100 having a top plate 108 disposed within an opening in a main body 102, the opening being smaller than the size of the top plate.

As shown in FIG. 9, in an assembled configuration, intraocular drainage device 100 may have a top plate 108 that is secured within a recess in main body 102 by lobes 900 of the main body that extend over a portion of the top surface of the top plate. Opening 901, having a size that is smaller than the size of top plate 108, may be resiliently stretchable to allow top plate 108 to be inserted through opening 901. Lobes 900 may help secure top plate 108 within main body 102.

FIG. 10 shows an example of the intraocular drainage device 100 of FIG. 10 in situ on the sclera 400 of a patient's eye with tube 106 extending through the sclera into the anterior chamber of the eye behind the cornea 406. In the perspective view of FIG. 10, it can be seen that only a portion 154' of the top surface of top plate 108 is exposed within opening 901 in main body 102 while other portions of the top surface are covered by lobes 900. Lobes 900 may bear against the other portions of the top surface of top plate 108.

The top view of FIGS. 9 and 10 also show how each of arms 110 of main body 102 may be extend along and be separated from tube 106 by a gap 902. In this way, suture openings 112 may be formed nearer to the cornea 406 of the eye and arms 110 may be flexibly movable to conform to the features of the surface of the sclera 400. Conjunctival tissue that may be formed over device 100 in situ is not shown in FIG. 10 for clarity.

Figure 11:
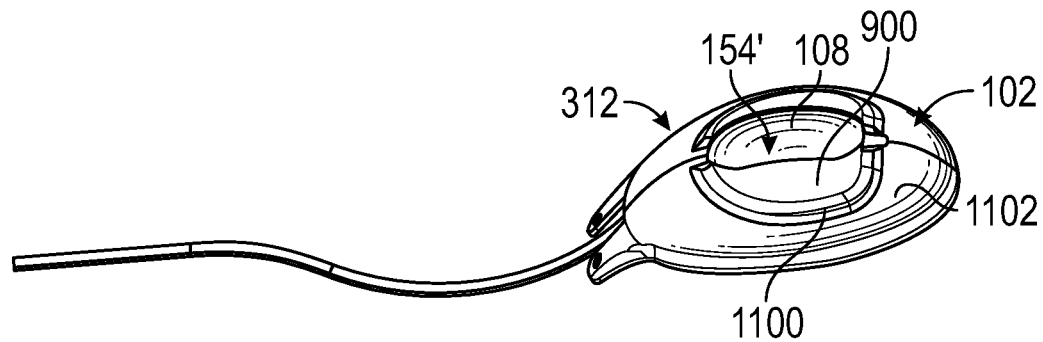
FIG. 11 shows a side perspective view of an intraocular drainage device, in accordance with one or more embodiments of the present disclosure.

FIG. 11 shows a side perspective view of the intraocular drainage device 100 of FIGS. 9 and 10 in which the convex top surface 312, formed by lobes 900, portion 154' of top plate 108, and shelf 1102 of main body 102, can be seen. In the examples of FIGS. 9-11, main body 102 includes step 1100 between shelf 1102 and lobes 900.

Figure 12:
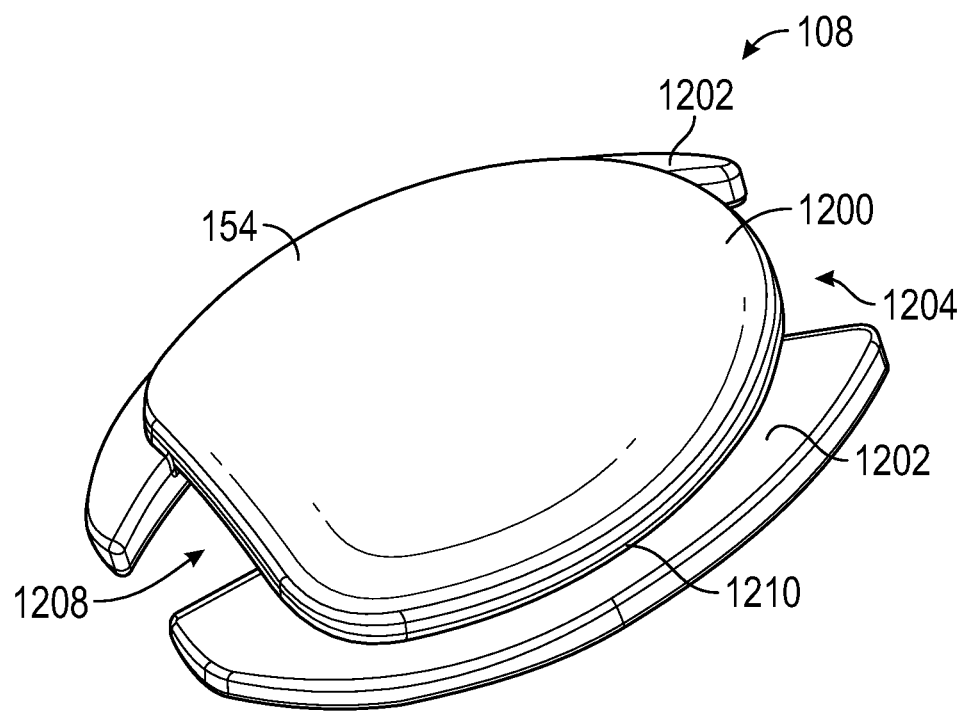
FIG. 12 shows a top perspective view of a top plate for an intraocular drainage device, in accordance with one or more embodiments of the present disclosure.

As shown in FIG. 12, in some implementations, top plate 108 may be implemented with a step 1210 that fits into the step 1100 in main body 102. In the example of FIG. 12, top plate 108 also includes shelf members 1202 disposed on opposing sides of a central portion 1200. Shelf members 1202 may be disposed underneath corresponding portions of shelf 1102 of FIG. 11 in an assembled configuration of device 100. As shown, shelf members 1202 may be separated by a gap 1204 at a front end of top plate 108 and by a gap 1208 at a rear end of top plate 108. Gap 1204 may be larger than gap 1208. Gap 1204 may accommodate a portion of tube 106. Gap 1208 may allow fluid (e.g., aqueous humour) to flow therethrough.

Figure 13:
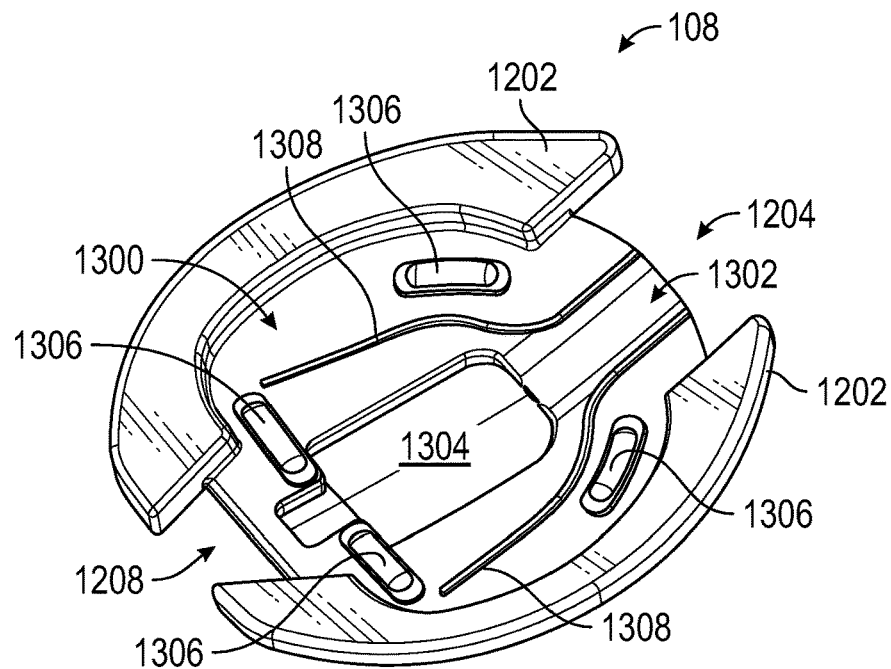
FIG. 13 shows a bottom perspective view of a top plate for an intraocular drainage device, in accordance with one or more embodiments of the present disclosure.

FIG. 13 is a bottom view of top plate 108 of FIG. 12. As shown in FIG. 13, a recess 1300 may be formed between shelf members 1202 on the underside of top plate 108. Various structural features may be formed on the underside of top plate 108 within recess 1300. As shown in FIG. 13, the structural features may include ridges 1306 configured to be attached (e.g., ultrasonically welded) to bottom plate 200 to attach top plate 108 to bottom plate 200. The structural features may also include a channel 1302 configured to receive a corresponding feature 222 of main body 102 within which a portion of tube 106 is disposed in an assembled configuration. The structural features may also include a widened channel 1304, which may form at least a portion of chamber 302 into which flap 214 can be raised by aqueous humor below the flap. The structural features may also include ridges 1308 that help to secure and control the raising of flap 214.

Figure 14:
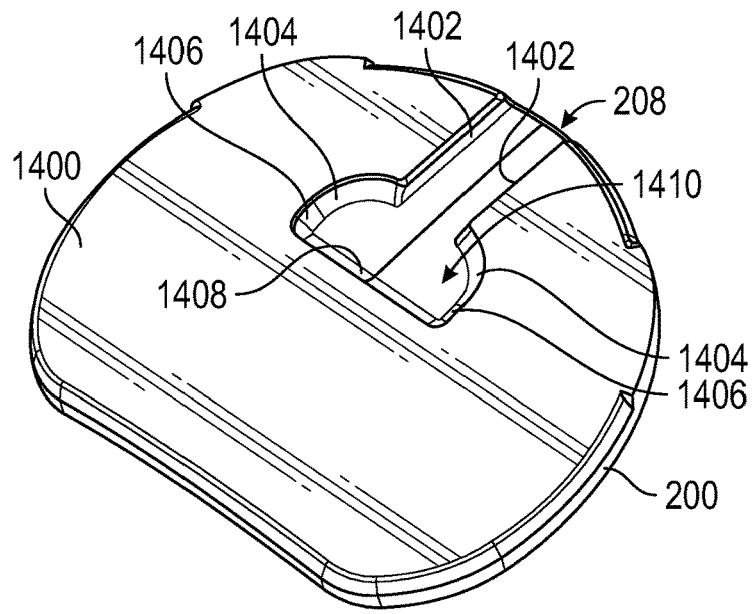
FIG. 14 shows a top perspective view of a bottom plate for an intraocular drainage device, in accordance with one or more embodiments of the present disclosure.

FIG. 14 shows a top perspective view of bottom plate 200 in an implementation that may be used, for example, with top plate 108 of FIGS. 9-13. As shown in FIG. 14, top surface 1400 of bottom plate 200 may be substantially free of ridges such as ridges 206 of FIG. 2. In such an implementation, ridges 1306 of top plate 108 may be attached directly to surface 1400 to secure top plate 108 to bottom plate 200. In an assembled configuration for intraocular drainage device 100, flap 214 may bear against surface 1400 until fluid pressure from aqueous humor from tube 106 raises the flap to separate the flap from surface 1400 to allow the aqueous humour to flow between surface 1400 and flap 214. As shown in FIG. 14, channel 208 may include a first portion having substantially parallel sidewalls 1402 and configured to receive a portion of tube 106. Channel 208 may also include an expanded portion 1410 formed by sidewalls 1404 that run away from each other on opposing sides of channel 208 in a curve that connects to additional substantially parallel portions 1406 spaced further apart than parallel sidewalls 1402. Substantially parallel portions 1406 of the sidewalls of expanded portions 1406 may meet with a transverse sidewall 1408 that runs between sidewalls 1406 substantially linearly in a direction perpendicular to sidewalls 1406. Sidewalls 1402 may be substantially planar sidewalls formed at a substantially perpendicular angle to surface 1400 or may be concave sidewalls having a shape that conforms to the shape of a portion of tube 106. Sidewalls 1404 and 1406 may be curved sidewalls as shown.

Expanded portion 1410 may form chamber 304 (see, e.g., FIG. 3) beneath flap 214. When fluid pressure within chamber 304 (e.g., due to aqueous humor received in expanded portion 1410 of channel 208 from the anterior chamber of a patient's eye via lumen 300) reaches a predetermined pressure threshold, the portion of flap 214 that is seated against surface 1400 of bottom plate 200 may be moved away from bottom plate 200 to allow fluid to flow therebetween. Providing a channel 208 with an expanded portion 1410 may provide a larger surface area on flap 214 for the fluid to bear against to lift the flap to allow fluid flow.

Figure 15:
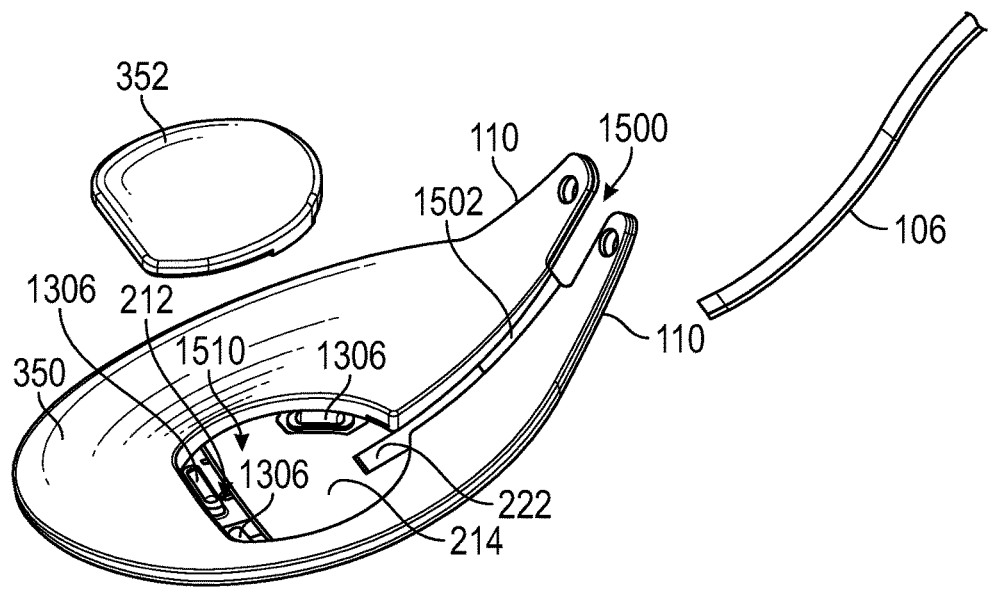
FIG. 15 shows a partially exploded bottom perspective view of an intraocular drainage device, in accordance with one or more embodiments of the present disclosure.

Concave bottom surface 352 of bottom plate 200 of FIG. 14 can be seen in the partially exploded perspective view of intraocular drainage device 100 in FIG. 15. As shown, concave bottom surface 352 of bottom plate 200 and concave bottom surface 350 of main body 102 may form a concave bottom surface for intraocular drainage device 100 when bottom plate 200 is placed into opening 1510 in the bottom surface of main body 102 and bonded to top plate 108.

As shown in FIG. 15, ridges 1306 on top plate 108 extend through openings in flap 214 so that they can mate with surface 1400 of bottom plate 200 when bottom plate 200 is inserted into opening 1510. FIG. 15 also shows a channel 1502 in main body 102 that extends from a gap 1500 between arms 110 continuously to recess 222 for receiving tube 106.

Figure 16:
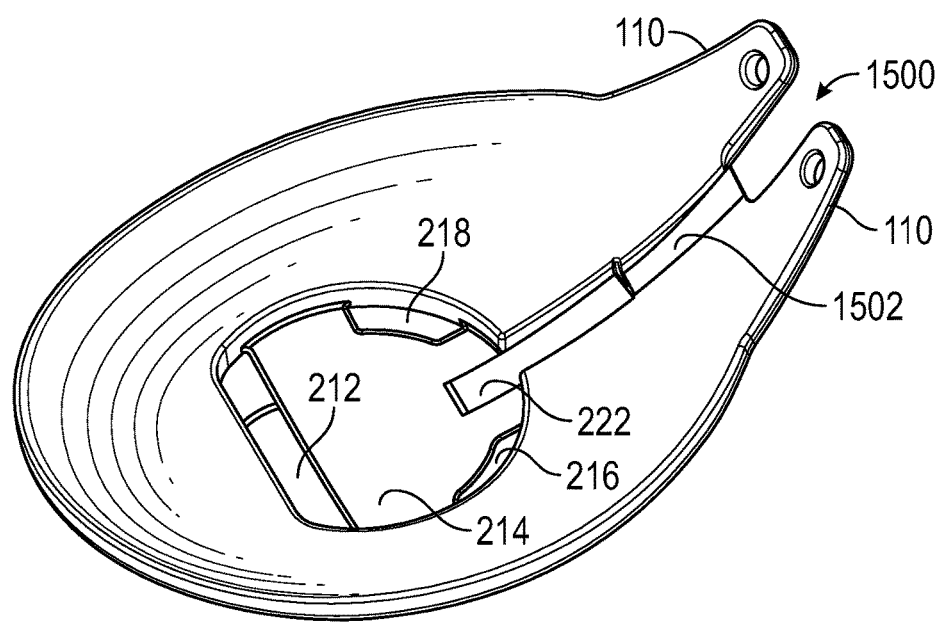
FIG. 16 shows a bottom perspective view of a main body for an intraocular drainage device, in accordance with one or more embodiments of the present disclosure.

FIG. 16 shows an enlarged bottom perspective view of main body 102 in which openings 212, 216 and 218, through which ridges 1306 can pass, can be seen. Opening 212 may also form a portion of a fluid pathway for aqueous humor when flap 214 is raised away from surface 1400 of bottom plate 200.

Figure 17:
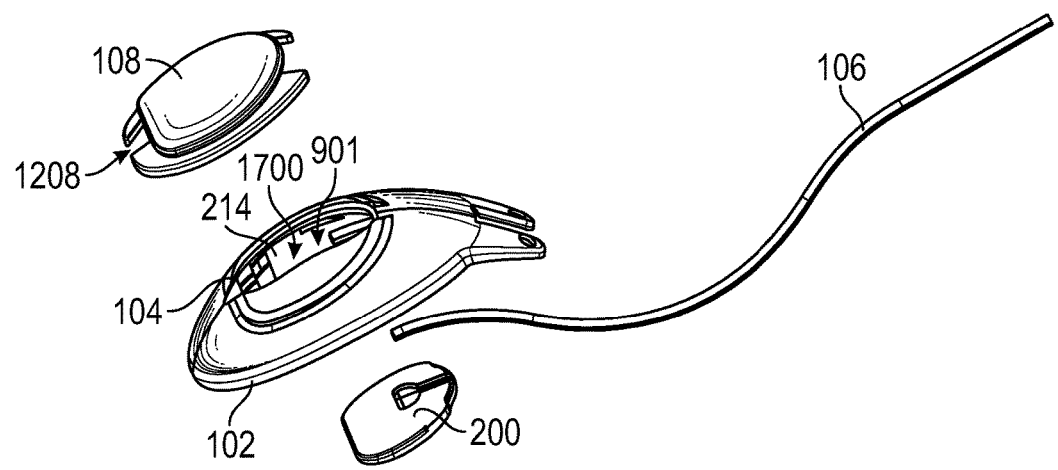
FIG. 17 shows an exploded top perspective view of an intraocular drainage device, in accordance with one or more embodiments of the present disclosure.

FIG. 17 shows a top exploded perspective view of intraocular drainage device 100 in accordance with various aspects. In the example of FIG. 17, top plate 108 of FIGS. 12 and 13 and bottom plate 200 of FIG. 14 are implemented with a main body 102 having an opening 901 that is smaller than the size of top plate 108. To assemble intraocular drainage device 100, top plate 108 is inserted into opening 901 and positioned such that shelf members 1202 and step 1210 of top plate 108 are disposed against corresponding shelf portions 1102 and step 1100 of main body 102 and such that ridges 1306 of top plate 108 extend through openings 212, 216 and 218 in flap 214. Tube 106 is placed into recess 1502 and 222 in main body 102 and bottom plate 200 is placed into opening 1510 in main body 102 such that surface 1400 of bottom plate 200 abuts ridges 1306. Ridges 1306 are then bonded (e.g., adhesively bonded, mechanically bonded, or ultrasonically welded) to surface 1400 of bottom plate 200 to secure top plate 108 to bottom plate 200 and thereby secure main body 102, flap 214, and tube 106 between top plate 108 and bottom plate 200. Top surface 1700 may be lifted into recess 1304 of top plate 108 by pressure generated by aqueous humour from tube 106.

Figure 18:
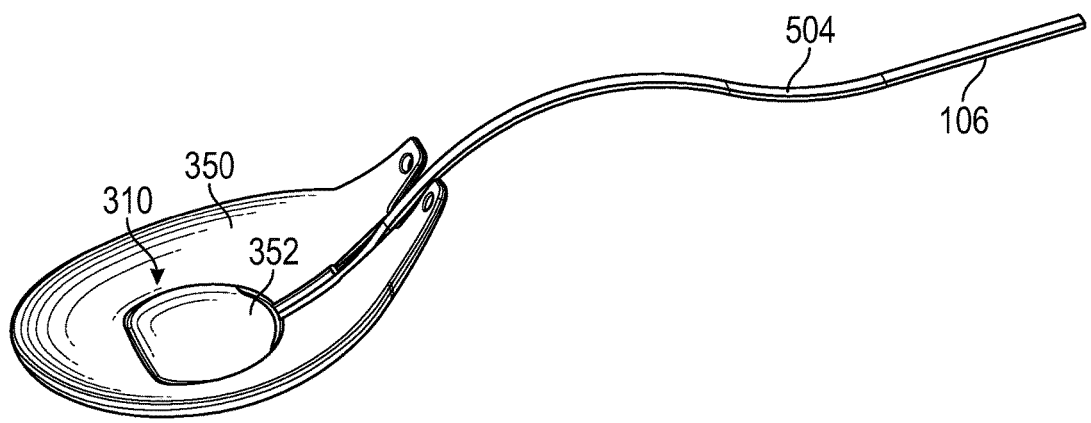
FIG. 18 shows a bottom perspective view of an intraocular drainage device, in accordance with one or more embodiments of the present disclosure.

A bottom perspective view of a fully assembled intraocular drainage device 100 is shown in FIG. 18 in accordance with some aspects of the subject disclosure. As shown in FIG. 18, the bottom surface of intraocular drainage device 100 is shaped and arranged to conform to the sclera of a patient's eye in situ. In particular, the concave bottom surface 350 of main body 102 and the concave bottom surface 352 of bottom plate 200 cooperate to form a substantially continuous concave bottom surface for intraocular drainage device 100 in which main body 102 is flexible to conform to the surface of the sclera. Additionally, as shown in FIG. 18, tube 106 may have a substantially flat bottom surface 504 that provides an increased surface area of contact with the underlying sclera of the eye and reduces the contact pressure relative to a round bottomed tube.

As noted above in connection with, for example, FIGS. 6-8, the outer surfaces of intraocular drainage device 100 may include microgrooves. Microgrooves may be formed, for example, on portion 154' of the top surface of top plate 108 of FIGS. 9-13. Microgrooves may be formed on bottom surfaces 350 and 352 of main body 102 and bottom plate 200. Microgrooves may be formed on a main body 102 having an opening 210 that is sized and configured to match the size and shape of top plate 108 or on a main body 102 having an opening 901 and lobes 900 in an arrangement as described above in connection with FIGS. 7 and 8. Microgrooves may be formed on shelf portion 1102, step 1100, lobes 900 and/or any other surface such as sidewall surfaces of main body 102 (e.g., as described above in connection with FIGS. 7 and 8).

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. An intraocular drainage device, comprising:
a monolithic silicone body having a flap;
a rigid bottom plate having a portion configured to contact a corresponding portion of the flap; and
a tube having a proximal end disposed between the flap and the rigid bottom plate, wherein the corresponding portion of the flap is configured to separate from the portion of the rigid bottom plate responsive to a pressure of aqueous humor received from the tube.

Concept 2. The intraocular drainage device of Concept 1 or any other Concept, wherein the tube comprises a distal end configured to be disposed within an anterior chamber of an eye of a patient.

Concept 3. The intraocular drainage device of Concept 2 or any other Concept, wherein the tube is configured to extend through a portion of a sclera of the eye of the patient at a location between the proximal end and the distal end.

Concept 4. The intraocular drainage device of Concept 1 or any other Concept, further comprising a chamber disposed between an additional portion of the flap and an additional corresponding portion of the rigid bottom plate.

Concept 5. The intraocular drainage device of Concept 4 or any other Concept, wherein a lumen of the tube is fluidly coupled to the chamber at the proximal end.

Concept 6. The intraocular drainage device of Concept 5 or any other Concept, wherein the rigid bottom plate comprises a first channel adjacent the chamber.

Concept 7. The intraocular drainage device of Concept 6 or any other Concept, wherein the flap comprises a recess configured to receive a portion of the tube.

Concept 8. The intraocular drainage device of Concept 7 or any other Concept, wherein the additional corresponding portion of the flap defines a portion of the chamber and is disposed between the portion of the flap that contacts the rigid bottom plate and the recess.

Concept 9. The intraocular drainage device of Concept 8 or any other Concept, wherein the rigid bottom plate comprises a second channel, wherein the first channel is disposed on a first side of the portion of the flap and wherein the second channel is disposed on an opposing second side of the flap.

Concept 10. The intraocular drainage device of Concept 9 or any other Concept, further comprising a rigid top plate.

Concept 11. The intraocular drainage device of Concept 10 or any other Concept, wherein the rigid top plate comprises a channel disposed opposite the second channel of the bottom plate.

Concept 12. The intraocular drainage device of Concept 11 or any other Concept, wherein the monolithic silicone body comprises an opening adjacent an exit port, the exit port formed by the channel of the top plate and the opposing second channel of the bottom plate.

Concept 13. The intraocular drainage device of Concept 12 or any other Concept, wherein the opening comprises a slot.

Concept 14. The intraocular drainage device of Concept 1 or any other Concept, wherein the tube has a D-shaped cross-sectional profile.

Concept 15. The intraocular drainage device of Concept 14 or any other Concept, wherein tube comprises a lumen that has a corresponding D-shaped cross-sectional profile.

Concept 16. The intraocular drainage device of Concept 1 or any other Concept, further comprising a rigid top plate.

Concept 17. The intraocular drainage device of Concept 16 or any other Concept, wherein the rigid bottom plate is sealingly disposed within an opening in a bottom surface of the monolithic silicone body.

Concept 18. The intraocular drainage device of Concept 17 or any other Concept, wherein the rigid top plate is sealingly disposed within an opening in a top surface of the monolithic silicone body.

Concept 19. The intraocular drainage device of Concept 18 or any other Concept, wherein the rigid top plate and rigid bottom plate engaged at one or more locations via one or more corresponding openings in the flap.

Concept 20. The intraocular drainage device of Concept 16 or any other Concept, wherein the rigid bottom plate is plastic.

Concept 21. The intraocular drainage device of Concept 20 or any other Concept, wherein the rigid top plate is plastic.

Concept 22. The intraocular drainage device of Concept 21 or any other Concept, wherein the plastic comprises polysulfone.

Concept 23. The intraocular drainage device of Concept 1 or any other Concept, further comprising a plurality of parallel microgrooves on at least a portion of an outer surface of the monolithic silicone body.

Concept 24. The intraocular drainage device of Concept 23 or any other Concept, further comprising a plurality of microgrooves on the rigid bottom plate.

Concept 25. The intraocular drainage device of Concept 24 or any other Concept, further comprising:
- a rigid top plate disposed in an opening in the monolithic silicone body; and
- a plurality of microgrooves on the rigid top plate.

Concept 26. The intraocular drainage device of Concept 23 or any other Concept, wherein the plurality of parallel microgrooves comprises parallel microgrooves formed on a top surface, a bottom surface, and a sidewall surface of the monolithic silicone body.

Concept 27. An intraocular drainage device, comprising:
- a main body having a channel;
- a flap disposed within the main body;
- a rigid bottom plate having a portion configured to contact a corresponding portion of the flap; and
- a tube bonded to the main body such that the channel is configured to guide fluid from the tube to a chamber formed adjacent the flap, wherein the corresponding portion of the flap is configured to separate from the portion of the rigid bottom plate responsive to a pressure of the fluid in the chamber.

Concept 28. An intraocular drainage device, comprising:
- a main body;
- a flow control device within the main body operable to allow fluid flow through the main body in a fluid flow direction; and
- a plurality of microgrooves formed on an outer surface of the main body, the plurality of microgrooves being arranged in parallel rows and extending substantially parallel to the fluid flow direction from a front end to a back end of the main body.

Concept 29. The intraocular drainage device of Concept 28 or any other Concept, wherein the plurality of microgrooves include parallel rows of microgrooves on a top surface of the main body.

Concept 30. The intraocular drainage device of Concept 29 or any other Concept, wherein the plurality of microgrooves further include parallel rows of microgrooves on a bottom surface of the main body.

Concept 31. The intraocular drainage device of Concept 30 or any other Concept, wherein the plurality of microgrooves further include parallel rows of microgrooves on a sidewall surface of the main body.

Concept 32. The intraocular drainage device of Concept 31 or any other Concept, wherein the parallel rows of microgrooves on the sidewall surface of the main body comprise circumferential microgrooves that extend around at least a portion of the circumference of the main body.

Concept 33. The intraocular drainage device of Concept 28 or any other Concept, wherein the parallel rows of microgrooves are each separated by approximately 25 microns.

Concept 34. The intraocular drainage device of Concept 28 or any other Concept, wherein the main body comprises a flexible main body, wherein the flow control device comprises a valve formed in part by a flap portion of the flexible main body, and wherein the device further comprises:
- a rigid top plate and a rigid bottom plate each disposed in a respective opening on the flexible main body; and
- a plurality of microgrooves extending substantially parallel to the fluid flow direction on each of the rigid top plate and the rigid bottom plate.

Concept 35. An intraocular drainage device, comprising:
- a flexible main body having a flap and a top surface having an opening bounded by opposing lobes;
- a rigid bottom plate having a portion configured to contact a corresponding portion of the flap; and
- a rigid top plate disposed in the opening in the top surface of the flexible main body, wherein a portion of the top surface of the rigid top plate in the opening forms a portion of a top surface of the device and wherein the opposing lobes each bear against another portion of the top surface of the rigid top plate.

Concept 36. The intraocular drainage device of Concept 35 or any other Concept, wherein the rigid top plate comprises a central portion and a pair of shelf members disposed on opposing sides of the rigid top plate.

Concept 37. The intraocular drainage device of Concept 36 or any other Concept, wherein the rigid top plate comprises a step disposed between the pair of shelf members and the top surface of the rigid top plate and wherein the flexible main body includes a step that conforms to the step on the rigid top plate.

Concept 38. The intraocular drainage device of Concept 35 or any other Concept, further comprising a tube having a proximal end disposed between the flap and the rigid bottom plate, wherein the corresponding portion of the flap is configured to separate from the portion of the rigid bottom plate responsive to a pressure of aqueous humor received from the tube.

Concept 39. The intraocular drainage device of Concept 38 or any other Concept, wherein the tube comprises a distal end configured to be disposed within an anterior chamber of an eye of a patient.

Concept 40. The intraocular drainage device of Concept 35 or any other Concept, wherein the flexible main body comprises a monolithic silicone body.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. Any accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An intraocular drainage device, comprising:
   a monolithic silicone body having a flap;
   a rigid bottom plate having a portion configured to contact a corresponding portion of the flap; and
   a tube having a proximal end disposed between the flap and the rigid bottom plate, wherein the corresponding portion of the flap is configured to separate from the portion of the rigid bottom plate responsive to a pressure of aqueous humor received from the tube.

2. The intraocular drainage device of claim 1, wherein the tube comprises a distal end configured to be disposed within an anterior chamber of an eye of a patient, and wherein the tube is configured to extend through a portion of a sclera of the eye of the patient at a location between the proximal end and the distal end.

3. The intraocular drainage device of claim 1, further comprising a chamber disposed between an additional portion of the flap and an additional corresponding portion of the rigid bottom plate.

4. The intraocular drainage device of claim 3, wherein a lumen of the tube is fluidly coupled to the chamber at the proximal end.

5. The intraocular drainage device of claim 4, wherein the rigid bottom plate comprises a first channel adjacent the chamber.

6. The intraocular drainage device of claim 5, wherein the flap comprises a recess configured to receive a portion of the tube.

7. The intraocular drainage device of claim 6, wherein the additional corresponding portion of the flap defines a portion of the chamber and is disposed between the portion of the flap that contacts the rigid bottom plate and the recess.

8. The intraocular drainage device of claim 7, further comprising a rigid top plate.

9. The intraocular drainage device of claim 1, wherein the tube has a D-shaped cross-sectional profile.

10. The intraocular drainage device of claim 1, further comprising a rigid top plate, wherein the rigid bottom plate is sealingly disposed within an opening in a bottom surface of the monolithic silicone body and the rigid top plate is sealingly disposed within an opening in a top surface of the monolithic silicone body.

11. The intraocular drainage device of claim 10, wherein the rigid top plate and rigid bottom plate are engaged at one or more locations via one or more corresponding openings in the flap.

12. The intraocular drainage device of claim 1, further comprising a plurality of parallel microgrooves on at least a portion of an outer surface of the monolithic silicone body.

13. The intraocular drainage device of claim 12, further comprising a plurality of microgrooves on the rigid bottom plate.

14. The intraocular drainage device of claim 13, further comprising:
   a rigid top plate disposed in an opening in the monolithic silicone body; and
   a plurality of microgrooves on the rigid top plate.

15. The intraocular drainage device of claim 14, wherein the plurality of parallel microgrooves comprises parallel microgrooves formed on a top surface, a bottom surface, and a sidewall surface of the monolithic silicone body.

16. An intraocular drainage device, comprising:
a main body having a channel;
a flap disposed within the main body;
a rigid bottom plate having a portion configured to contact a corresponding portion of the flap; and
a tube bonded to the main body such that a proximal end of the tube is disposed between the flap and the rigid bottom plate and such that the channel is configured to guide fluid from the tube to a chamber formed adjacent the flap, wherein the corresponding portion of the flap is configured to separate from the portion of the rigid bottom plate responsive to a pressure of the fluid in the chamber.

* * * * *

UNITED STATES PATENT AND TRADEMARK OFFICE
CERTIFICATE OF CORRECTION

PATENT NO. : 10,154,925 B2  
APPLICATION NO. : 15/613021  
DATED : December 18, 2018  
INVENTOR(S) : Abdul Mateen Ahmed et al.

Page 1 of 1

It is certified that error appears in the above-identified patent and that said Letters Patent is hereby corrected as shown below:

On the Title Page

Below Abstract, replace "16 Claims, 9 Drawing Sheets" with --12 Claims, 9 Drawing Sheets--.

In the Claims

In Column 18, Line 53, cancel the text beginning with "12. The intraocular drainage device" and ending with "a sidewall surface of the monolithic silicone body." in Column 18, Line 67.

In Column 19, Line 1, replace "16. An intraocular drainage device" with --12. An intraocular drainage device--.

Signed and Sealed this  
Eighteenth Day of June, 2019

Andrei Iancu  
*Director of the United States Patent and Trademark Office*